US00PP26161P3

(12) United States Plant Patent
Shipley

(10) Patent No.: US PP26,161 P3
(45) Date of Patent: Nov. 24, 2015

(54) ***GAURA* PLANT NAMED 'MR. LIKO'**

(50) Latin Name: *Gaura lindheimeri*
Varietal Denomination: Mr. Liko

(71) Applicant: Nicholas Shipley, Tucson, AZ (US)

(72) Inventor: Nicholas Shipley, Tucson, AZ (US)

( * ) Notice: Subject to any disclaimer, the term of this patent is extended or adjusted under 35 U.S.C. 154(b) by 118 days.

(21) Appl. No.: 13/986,096

(22) Filed: Apr. 1, 2013

(65) Prior Publication Data

US 2014/0298555 P1 Oct. 2, 2014

(51) Int. Cl.
*A01H 5/02* (2006.01)

(52) U.S. Cl.
USPC ..... Plt./432
CPC ..... *A01H 5/02* (2013.01)

(58) Field of Classification Search
USPC ..... Plt./432
See application file for complete search history.

(56) References Cited

PUBLICATIONS

Civano Nursery, *Gaura lindheimeri* Mr Liko (retrieved from the internet on Mar. 19, 2014), one page.*

* cited by examiner

*Primary Examiner* — Keith O. Robinson

(57) ABSTRACT

A new and distinct *Gaura lindheimeri* named Mr. Liko is characterized by its compact, shrubby form, light pink flowers with nearly ever blooming tendencies.

3 Drawing Sheets

Latin name: *Gaura lindheimeri.*
Varietal denomination: Mr. Liko.

BACKGROUND OF THE INVENTION

The plant family Onagraceae contains several genera of plants that have value as ornamental flowering perennials including *Fuchsia, Oenothera* and *Gaura*. The genus *Gaura* garnered little attention as a plant useful for ornamental horticulture until the 1980's. In 1994 the first of many selections of *Gaura lindheimeri* appeared in commerce. Since then many cultivars have been created, and this plant is now a common landscape plant throughout much of the world with moderate-warm climates. Many of the current cultivars become leggy and floppy with age, becoming less attractive and requiring pruning to maintain a tidy form.

The present invention relates to a new and distinct cultivar of *Gaura lindheimeri*. This new cultivar originated in a cultivated area of a commercial nursery near Tucson, Ariz. as a bud sport of the unpatented cultivar 'Pink Cloud'. The new cultivar exhibits strongly shrubby tendencies as well as having light pink flowers and increased floriferousness and is the object of this application.

SUMMARY OF THE INVENTION

Among the features that distinguish the new cultivar from all other available and commercial varieties of *Gaura lindheimeri* known to the inventor are the following combination of characteristics: compact, shrubby growth form, light pink flowers, long flowering period, and heavy bloom production. *Gaura lindheimeri* 'Mr. Liko' will be used as a flowering ornamental both in the landscape and in containers.

The propagation procedure is as follows: Two and one half to three inch long stem cuttings are prepared containing 3-4 nodes. Leaves are removed from the basal node. Stems are immersed in DIP'N GROW™, a liquid, auxin based rooting hormone solution, then planted in rooting media and placed into a mist propagation greenhouse with 65° F. minimum bottom heat and 85-95% relative humidity. Cuttings are rooted in about 3 weeks.

The foregoing characteristics and distinctions come true to form and are established and transmitted through succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Gaura lindheimeri* 'Mr. Liko' growing near Tucson, Ariz., depicted in color as nearly correct as it is possible to make in a color illustration of the character.

DETAILED PLANT DESRIPTION

Figure 1:
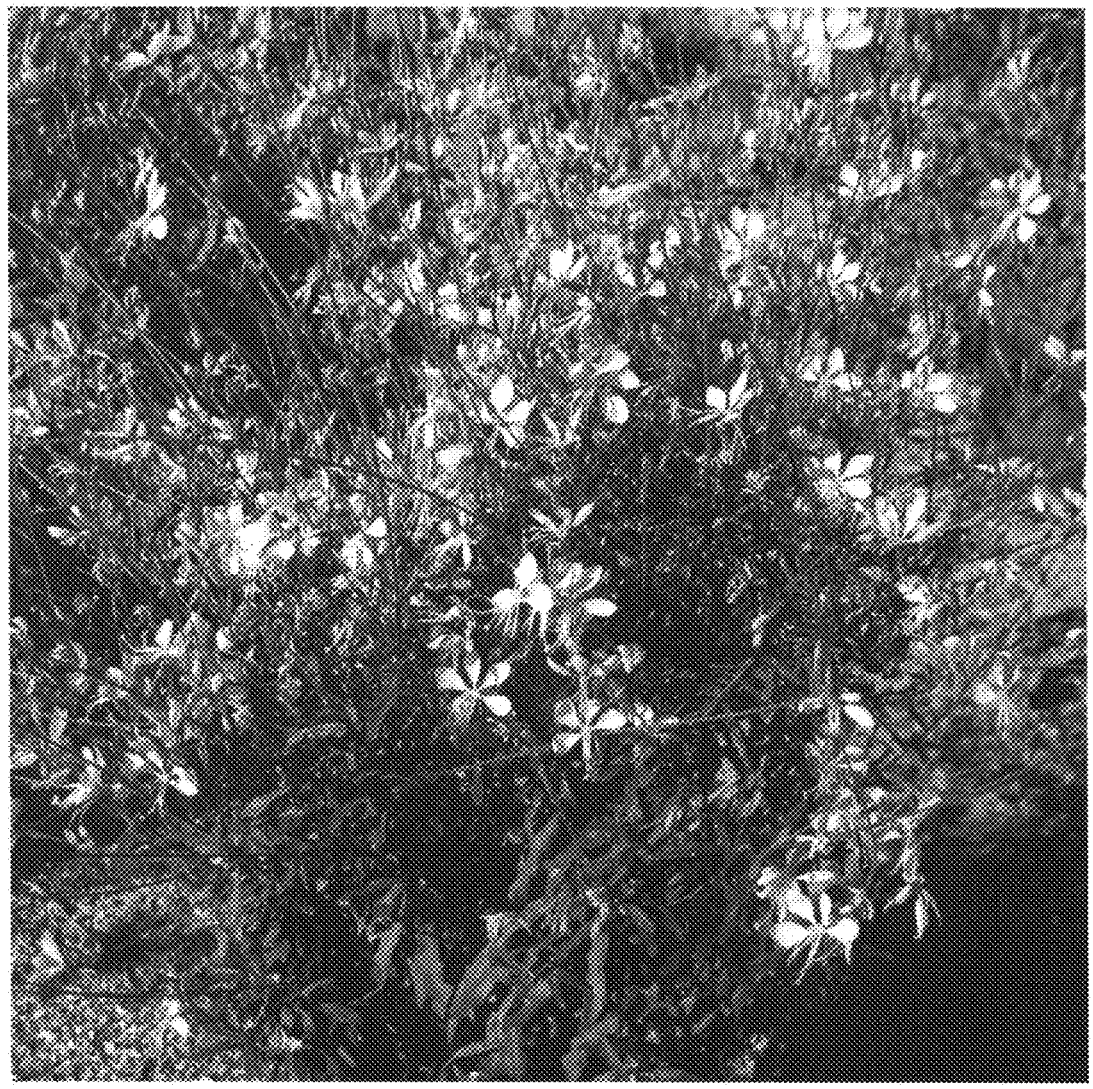
FIG. 1 shows *Gaura lindheimeri* 'Mr. Liko' plant.
Figure 2:
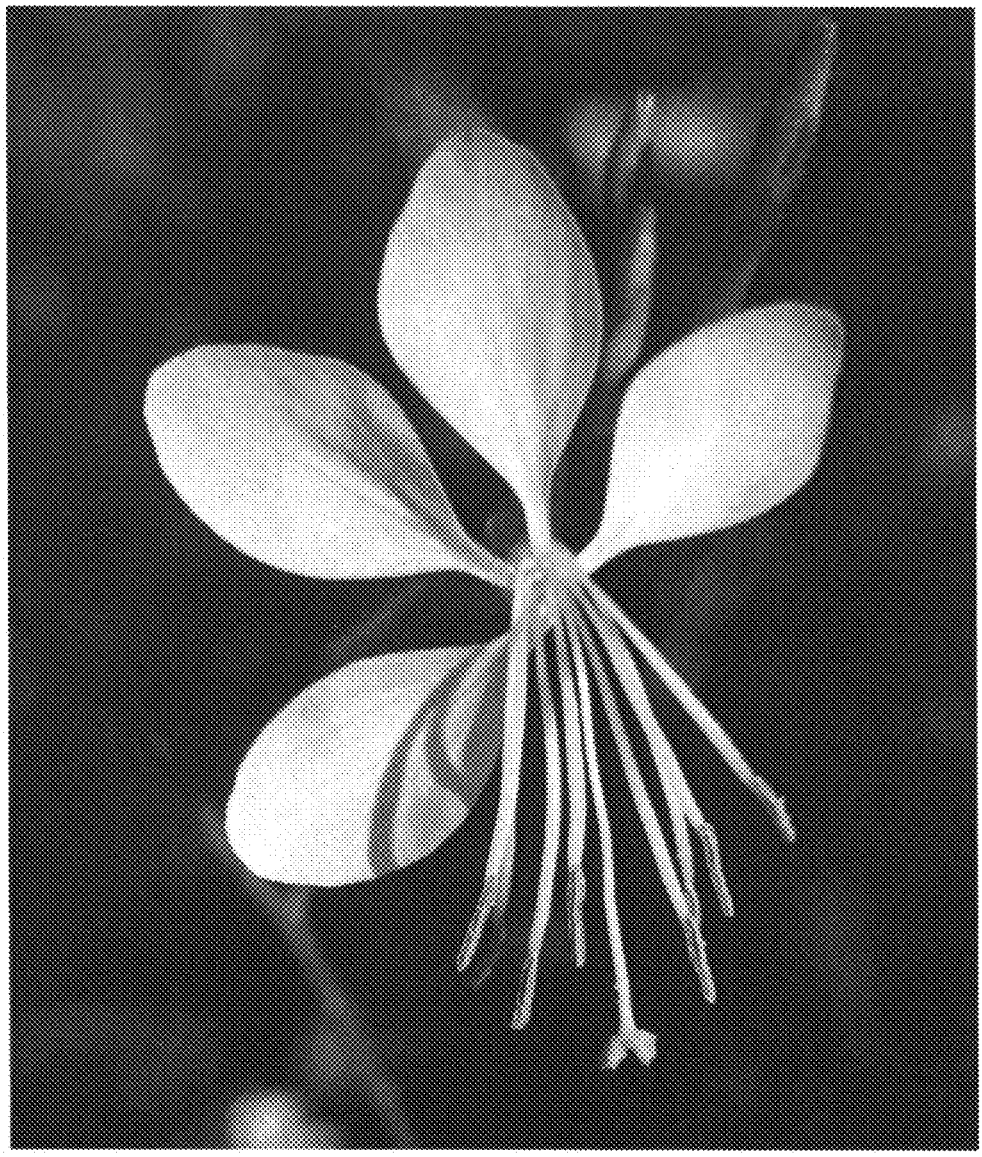
FIG. 2 is a closeup of a flower of 'Mr. Liko'.
Figure 3:
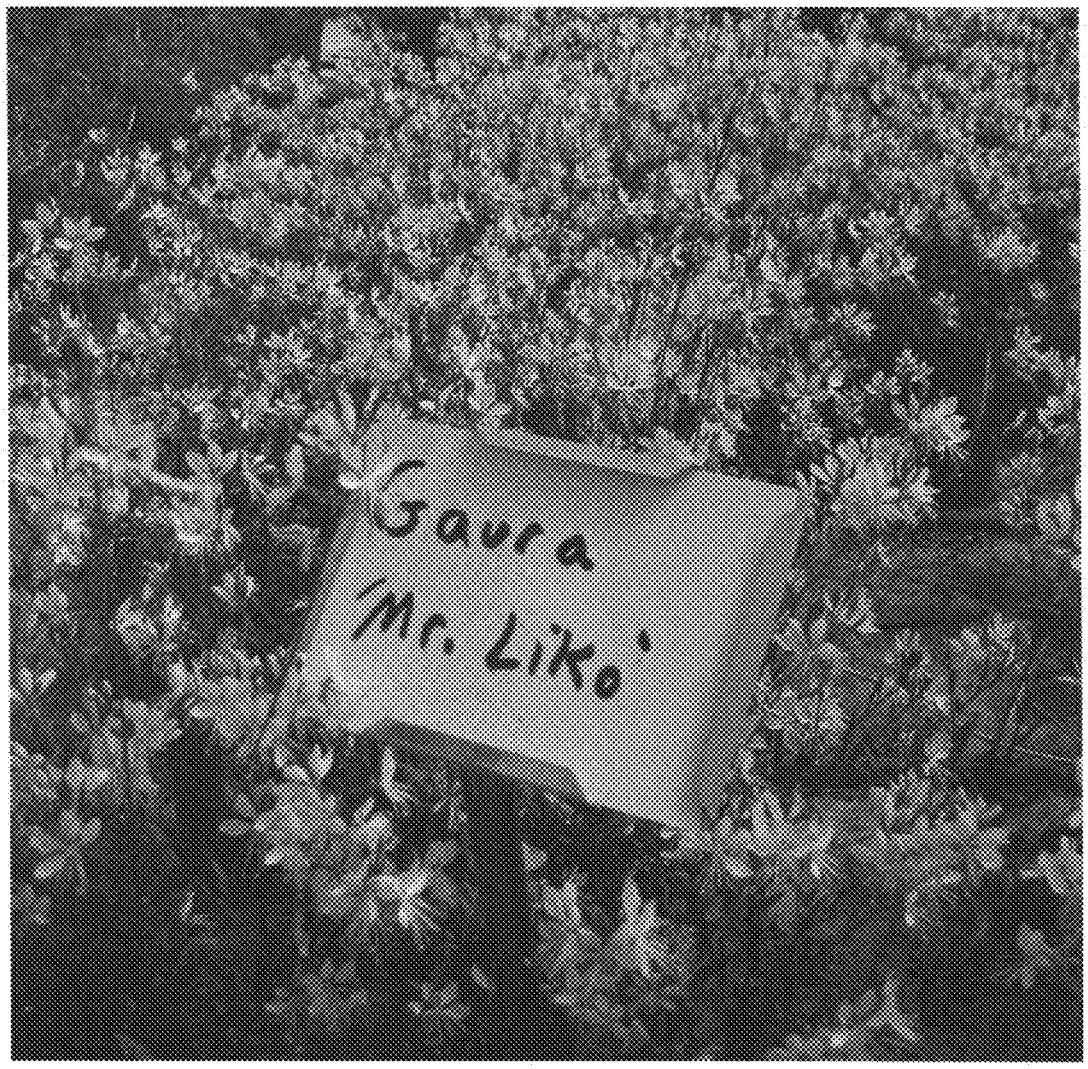
FIG. 3 shows a growout of plants from cuttings of 'Mr. Liko' in bloom, demonstrating the stability the variety.

The following plant measurements were taken from a container grown specimen. The color descriptions are based upon the 5$^{th}$ edition R.H.S. Colour Chart. Color names other than common usage are as listed in *COLOR Universal Language and Dictionary of Names*, by Kenneth L. Kelly and Deane B. Judd; National Bureau of Standards special publication 440. Washington, D.C.: U.S. Department of Commerce, National Bureau of Standards, December 1976.

*Gaura lindheimeri* 'Mr. Liko' is a highly branched suffrutescent shrub which ultimately grows to about 3½ feet tall by 3½ feet wide.

Stems: 7 mm diameter at base tapering to 1 mm in the upper parts of the inflorescence; older stems covered with longitudinally cracked, relatively smooth bark (165C); younger stems sparsely puberulent (color highly variable, including all colors from 137C to N77A, depending upon insolation, temperature and growth conditions); internode length varies from near zero length in spurs up to 42 mm along main axes. Branch angle varies from 40 to 60 degrees from the main axis.

Leaves: Alternate, oblanceolate/spatulate, highly variable in size from 2×7 mm to 11×55 mm, leaf margin puberulous on new leaves, becoming glabrate with age; leaf margin entire and obscurely toothed, margins flattish to somewhat downcurved, not enrolled; leaf color (both surfaces similar) (137B, with blotches of 59A).

Inflorescence: A spikate panicle, basally leafy, apically naked, sparsely puberulent, the axis tapering from 2 mm diameter to 1 mm apically (137B grading to N77A on sunward side and at nodes at the attachment region); 20 to 57 cm in length.

Flower buds just before anthesis: Oblanceoloid, 10-13 mm long×2.3-2.7 mm wide, surface (191B, with blotches and streaks of 185B especially near the base and tip)(abaxial calyx surface) puberulent with a mixture of relatively upright glandular hairs and somewhat apically appressed non-glandular hairs; internally, undehisced anthers 4 mm long×0.7 mm thick, basifixed, adaxially longitudinally dehiscent on two lines, adaxial surface glabrous (1B), abaxial surface glabrous 185A. Pollen color (3C).

Flowers: Tubular, bilabiate, reddening with age (descriptions and colors as seen in fresh flowers); stamens, petals and calyx all united at the limb of the tube.

*Tube*.—Ellipsoidal 4.5-5 mm long×1.3 mm wide sparsely puberulent externally (grading from 146B on shaded side to 185Aon the sunward side and on extensions of color striping from the ribs of the ovary).

*Ovary*.—Inferior, 5 mm long×1.2 mm diameter, long ellipsoidal, 4 ribbed, puberulent, the hairs mostly erect, with fewer hairs on the ribs, color 185A on sunward side and along ribs, 146B between ribs on the shaded side.

*Sepals*.—4, equal, linear, 11 mm long×1.7 mm wide, strongly reflexed at anthesis, spreading at tips, adaxially glabrous grading from 186D at limb to 194C at tips with a noticeable central line, color 186A, abaxially puberulent, color 186D.

*Petals*.—4, spreading, bilabiate, 2 angled upward, 2 lateral, clavate/obovate 14 mm long×7 mm wide, glabrous, somewhat cupped apically, color grading from 56D centrally to 56A on the petal margins, abaxial and adaxial surfaces and colors alike.

Stamens: 8, 13-15 mm long, cascading, anthers basifixed, filaments, 9-11 mm long×0.6 mm wide, whiter than 56D, anthers at anthesis 3 mm long×0.3 mm wide.

*Style/stigma*.—17 mm long×0.4 mm diameter, cascading more or less with stamens, color grades from 1D basally to 150B at stigma.

Stigma: 4 lobed, each lobe 1 mm long by 1.5 mm wide, ovoid, lobes increasingly spreading with age, color 150B.

Fruit: Apparently fairly sterile under our conditions, ovaries deciduous within a week after flowering.

Disease and insect notes: No disease or insect problems were noted on *Gaura* 'Mr. Liko' plants under our conditions. No testing regarding disease or insect resistance of 'Mr. Liko' was performed.

COMPARISONS TO RELATED *GAURA LINDHEIMERI*

Compared to its originating bud parent variety, 'Pink Cloud', flowers of 'Mr. Liko' are much lighter in color. Pink Cloud has strong red flowers (54A), while the flowers of 'Mr. Liko' are light pink (56D-56A). Plant form of both plants is indistinguishable. There appears to be a general reduction of anthocyanin production in 'Mr. Liko' compared to 'Pink Cloud', mostly during the warm season. Plant color during the cool season is similar in both cultivars. Mr. Liko appears to have increased floriferousness, compared to 'Pink Cloud'

I claim:

1. A new and distinct *Gaura lindheimeri* plant substantially as described and illustrated herein.

* * * * *